United States Patent [19]

Kay

[11] Patent Number: 5,830,932
[45] Date of Patent: Nov. 3, 1998

[54] EXTERNAL INCONTINENCE DEVICE AND VAPOR-ABSORPTIVE ADHESIVE COMPOSITIONS

[75] Inventor: Dennis M. Kay, Tampa, Fla.

[73] Assignee: BioDerm, Inc., St, Petersburg, Fla.

[21] Appl. No.: 745,201

[22] Filed: Nov. 8, 1996

Related U.S. Application Data

[60] Division of Ser. No. 156,619, Nov. 23, 1993, which is a continuation-in-part of Ser. No. 747,376, Aug. 20, 1991, Pat. No. 5,263,947.

[51] Int. Cl.$^6$ ..................................................... C08L 5/04
[52] U.S. Cl. ............................................. 524/24; 524/28
[58] Field of Search ........................................ 524/24, 28

[56] References Cited

U.S. PATENT DOCUMENTS

| | | | |
|---|---|---|---|
| 3,559,651 | 2/1971 | Moss | 604/349 |
| 3,835,857 | 9/1974 | Rogers, III et al. | 604/349 |
| 3,955,997 | 5/1976 | Sagane | 524/28 |
| 3,970,629 | 7/1976 | Izaki | 524/28 |
| 4,115,331 | 9/1978 | Tominaga | 524/28 |
| 4,140,760 | 2/1979 | Withington | 424/81 |
| 4,284,079 | 8/1981 | Adair | 128/295 |
| 4,356,819 | 11/1982 | Potaczek | 604/336 |
| 4,484,914 | 11/1984 | Brown | 604/180 |
| 4,534,762 | 8/1985 | Heyer | 604/180 |
| 4,600,001 | 7/1986 | Gilman | 128/156 |
| 4,626,250 | 12/1986 | Schneider | 604/349 |
| 4,640,688 | 2/1987 | Hauser | 604/352 |
| 4,759,354 | 7/1988 | Quarfoot | 128/156 |
| 4,767,411 | 8/1988 | Edmunds | 604/180 |
| 4,790,834 | 12/1988 | Austin | 604/349 |
| 4,855,335 | 8/1989 | Neperod | 523/11 |
| 4,869,269 | 9/1989 | Sharkan | 604/349 |
| 4,872,464 | 10/1989 | Loeb et al. | 604/352 |
| 4,901,375 | 2/1990 | Dahlgren | 4/144.3 |
| 4,904,247 | 2/1990 | Therriault et al. | 604/304 |
| 4,913,138 | 4/1990 | Yoshida et al. | 128/155 |
| 4,915,102 | 4/1990 | Kwiatek et al. | 128/156 |
| 4,973,320 | 11/1990 | Brenner et al. | 604/265 |
| 5,077,336 | 12/1991 | Nakashita | 524/28 |
| 5,087,252 | 2/1992 | Denard | 604/349 |
| 5,263,947 | 11/1993 | Kay | 604/331 |
| 5,456,745 | 10/1995 | Roreger | 106/128 |

FOREIGN PATENT DOCUMENTS

| | | |
|---|---|---|
| 34 21 568 | 12/1985 | Germany . |
| 3421568 A1 | 12/1985 | Germany . |
| 2 090 741 | 7/1982 | United Kingdom . |
| 2 090741 | 7/1982 | United Kingdom . |
| 81/03273 | 11/1981 | WIPO . |
| WO 81/03273 | 11/1981 | WIPO . |

*Primary Examiner*—Paul R. Michl
*Attorney, Agent, or Firm*—Foley & Lardner

[57] ABSTRACT

An external incontinence device which reduces or eliminates maceration, skin irritation, microbial skin infiltration and infection, and urinary tract infection associated with conventional urinary catheters and incontinence devices is provided. Devices of the invention comprise, in a plurality of configurations, a housing having an outlet conduit, and several alternative means for attaching the housing to a para-meatal genital surface, including a barrier disc comprising various adhesive and medically active substances which form an occlusive adhesive seal with the para-meatal surface. Adhesive leaves made of fluid-absorptive or fluid-permeable materials are provided to adhere the device to skin while permitting removal of moisture from the underlying skin surface, thus eliminating maceration. Vapor permeable adhesives on the interior surface of the attachment elements, and a microbial-barrier layer provided on inner surfaces of the several configurations of housings are also provided. Antimicrobial agents are provided on or within various elements of the invention to prevent microbial infiltration into the urethral meatus, thus reducing or eliminating the incidence of urinary tract infection. New compositions of matter are also provided, comprising biocompatible hydrocolloid adhesive formulations useful in producing barrier discs of the invention as well as wound care pads, wound dressings and adhesives for the attachment of wound dressings and other devices to intact skin, mucosal surfaces, wounds and diseased or damaged epidermis, dermis or subcutaneous tissue. The disclosed compositions include two-component biocompatible hydrocolloids that rapidly cure to a solid flexible adhesive.

15 Claims, 8 Drawing Sheets

EXTERNAL INCONTINENCE DEVICE AND VAPOR-ABSORPTIVE ADHESIVE COMPOSITIONS

This application is a divisional of application Ser. No. 08/156,619, filed Nov. 23, 1993 which is a continuation-in-part of Ser. No. 07/747,376 filed Aug. 20, 1991 now U.S. Pat. No. 5,263,947.

BACKGROUND OF THE INVENTION

Urinary incontinence, a common medical problem, is currently treated with condom catheters, invasive catheters, incontinence pads and diapers.

There are several problems associated with the current treatments, most prominent of which is a high incidence of infections. The incidence of urinary tract infections with indwelling invasive urinary catheters is well described in current medical literature. The presence of an invasive catheter in the urethra is thought to facilitate the infiltration of microorganisms. Microorganisms at the catheter entrance site ascend the catheter through the urethra into the urinary tract, thus resulting in infections.

The conventional condom catheter is essentially a sheath-like bag connected to a tube. This bag is usually attached to the penis by a circumferential adhesive band. Often the attachment is inadequate and the condom catheter falls off or leaks. In other cases, the circumferential adhesive band results in irritation or even strangulation of the penis. The condom catheter design presents no barrier to the infiltration of microorganisms into the urethra. Inside the bag, the moist environment is ideal for microorganism growth. Microorganisms growing in the moist environment in the bag can enter the urethra and proceed into the urinary tract causing urinary tract infections.

Incontinence pads or diapers, whether used on male or female patients, also contribute to the onset and severity of infections because the excreted urine and/or feces contained in these devices are excellent media for bacterial growth. Such bacteria can enter the urethra because, in long term care facilities, personnel are often unable to change patients' diapers as frequently as recommended by good medical practice.

The second problem associated with current incontinence treatments is particularly related to the condom catheter. The conventional condom catheter causes skin maceration and irritation. The epidermis is composed of dead cells which protect the underlying living dermis cells from physical and chemical irritation and from microbial invasion. Maceration refers to the problems associated with prolonged exposure of the epidermis to moisture. When epidermal cells are exposed to moisture for a sufficient period of time, they absorb water, swell, and slough off, thus exposing the physiologically active dermal layer to whatever chemical or microbial entities are present in the immediate environment.

Maceration occurs not only when the skin is exposed to water from external sources but also when moisture is trapped against the skin surface by a water-impermeable membrane. Skin continually emits water, particularly in the genital area. If the emitted water is trapped against the skin surface by a water-impermeable membrane and is not able to evaporate, then maceration occurs.

If maceration proceeds unabated, an inflammation of cellular and connective tissue caused by the failure of the epidermis, often occurs. This inflammation is often accompanied or followed by microbial invasion, causing a cellulitis or tissue infection. Microbial invasion causes further tissue inflammation and destruction. In severe cases of cellulitis, extensive tissue destruction, necrosis or gangrene ensues, necessitating removal of the gangrenous tissues or the entire affected limb. Clearly, maintaining skin dryness is necessary to prevent the onset of maceration and further degenerative states.

The conventional condom catheter functions as a bag of moisture surrounding the penis. The condom catheter does not allow the necessary evaporation of moisture from the skin surface. Not only do the walls of the condom trap the emitted moisture against the skin surface, but urination also adds to the moisture trapped inside the condom and contributes chemical irritants, such as urea, to the enclosed area. Thus, conventional condom catheters cause maceration and skin irritation.

The maceration and skin irritation caused by condom catheters make them physically uncomfortable, and patients routinely remove them, either deliberately or inadvertently while sleeping. In addition, macerated tissue is moist and loose. Adhesive, therefore, does not adhere well to macerated skin. Thus, adding a simple adhesive to the condom catheter does not help, because the condom catheter becomes loose or falls off of the patient due to maceration under the adhesive.

Others in the field have attempted to solve the problems associated with urinary incontinence. Denard, U.S. Pat. No. 5,087,252, discloses a catheter which is insertable into the urinary bladder of a human male through the penis and urethra for the withdrawal of urine from the urinary bladder. Denard comprises a support strap with an adhesive surface adapted for securing the strap to the penis and for preventing withdrawal of the invasive tubular element from the penis and urethra. The invention of Denard possesses all the inherent disadvantages inherent to other devices which are in invasive to a urethra. These include the inconvenience, pain, and irritation associated with insertion of the device, as well as the provision of a path for microbial infiltration into the urethra and bladder by way of the external and internal surfaces of the tubular element. Additional disadvantages of Denard stem from the non-vapor permeable nature of the adhesive surfaces of its strap and adhesive pad.

Dahlgren, U.S. Pat. No. 4,901,375, comprises a male urinal appliance formed of a plastic urinal bottle with a contoured neck and reservoir portions and an adjustable support belt for securing the bottle to a person. The device of Dahlgren is non-invasive to a urethra but it is bulky and inconvenient to wear, however, requiring the use of support straps for attachment to a belt disposed around the waist of the wearer. Dahlgren also possesses disadvantages inherent to its lack of a sealing element for sealing the device to a skin surface or urethral meatus. Because of this, and because of Dahlgren's general configuration, it maintains a moist and septic environment near the penis, thus providing an excellent environment for infection and maceration of penile skin surfaces.

Austin, U.S. Pat. No. 4,790,834, discloses an external single-use disposable male catheter comprising a pliable top plastic container having a closed end and an opening having a closure of an extensible vapor permeable material disposed for attaching and removing the device from the shaft of a penis. Because Austin is a bag-like device, however, it possesses all the disadvantages of other devices which retain urine and other moisture in close proximity to a penis. For this reason, Austin requires frequent attention and inspection. Accordingly, Austin is not suitable for uses in many circumstances, particularly those where the wearer is unconscious or incapable of determining the precise condition of the skin surfaces affected by the device.

Schneider, U.S. Pat. No. 4,626,250, discloses a male urinary incontinence collection system comprising a tubular sheath of thin elastic material with an elastic tapered internal sleeve which is stretched into a sealing engagement with the penile glans to provide a barrier which is intended to prevent liquid from migrating proximally toward the adhesive attachment between the cylindrical portion of the catheter and the penile shaft. Schneider requires the use of a separate adhesive pad element which must be applied to reside on the penile shaft proximal to the corona in an attempt to achieve a smooth annular surface for sealing the device to a penis. Because of these design shortcomings and the characteristics which result therefrom, Schneider is awkward to use, expensive to manufacture, and results in the retention of urine and moisture in close proximity to substantial portions of penile skin when in use.

Moss, U.S. Pat. No. 3,559,651, discloses a body-worn disposable urinal comprising a plurality of concentric telescopically mounted bags having open ends secured to a collar wherein the device is attached to a body through a collar surrounding the penis and a series of attachment straps disposed to affix the collar around the base of the penis and to one leg. The telescopically mounted bag elements of Moss thus surround a penis and retain urine and other moisture in close proximity to the penile skin. Because of this, Moss possesses all the disadvantages of other bag-like devices and is, accordingly, unsuitable for use in many situations.

Thus, there is a need in the medical arts for an external incontinence device which is not invasive to a urethra and which does not retain urine or other fluids in close proximity to genital skin surfaces.

SUMMARY OF THE INVENTION

It is therefore an object of the present invention to reduce or eliminate microbial infiltration and the resulting infections associated with the use of conventional urinary catheters, incontinence devices and pads and diapers.

Yet another object of the present invention is to avoid skin maceration and irritation associated with condom catheter, diaper and incontinence pad use.

An additional object of the present invention is to provide a more comfortable external incontinence device, thus increasing patient compliance.

Another object of the present invention is to provide an external incontinence device that can be worn for seven or more days.

In satisfying these and other objects, there has been provided, in accordance with one aspect of the present invention, an external incontinence device comprising a housing which presents an outer surface and an inner surface wherein the inner surface is adapted for attachment to a para-meatal surface surrounding a urethral meatus. The housing comprises an outlet conduit for fluid drainage which has an internal and an external end wherein the internal end penetrates through the inner surface of the housing but does not extend beyond the longest reach of the housing. Several means are provided for holding the housing in close approximation to the urethral meatus so that the internal end of the outlet conduit communicates freely with the meatus so that removal of urine, water vapor and other physiological fluids from the skin surrounding the para-meatal surface can occur to thus avoid skin maceration.

One means provided for holding the housing over the urethral meatus comprises an adhesive barrier disc having a housing mating surface, and a para-meatal contact surface, wherein the adhesive disc is provided on the inner surface of the housing, and wherein the disc surrounds the internal end of the conduit, and surrounds the urethral meatus.

In accordance with other aspects of the invention, the adhesive barrier disc provides an occlusive mechanical seal against contaminants. In additional embodiments, the adhesive disc comprises a microbial-barrier layer, provided on the para-meatal contact surface of the disc, the layer being a medically active substance which prevents microbial infiltration into the urethra. In some preferred embodiments of the invention, the barrier disc comprises a hydrocolloid which absorbs water and urine.

Additionally, the barrier disc can comprise a hydrocolloid formulated to adhere to the para-meatal surface and surround either a male urethral opening or a female urethral opening to occlusively seal against contaminants. The barrier disc can further comprise an adhesive layer to increase the secureness of the attachment to the para-meatal surface.

Further in accordance with the objects of the invention, the adhesive in the microbial-barrier layer is formulated to be moisture compatible and the outlet conduit may comprise an anti-microbial or an antiseptic coating provided on the inside surface of the outlet conduit such that microbial infiltration through the outlet conduit may be attenuated. The outlet conduit is provided with an integral adaptor on the external end, such that attachment of the outlet conduit to various tubing connectors is permitted.

In accordance with other aspects of the invention, other means for holding the housing over a urethral meatus are provided comprising at least one leaf connected to the housing, wherein each leaf has an interior surface and an exterior surface and each leaf is comprised of a fluid-absorptive substance or a fluid-permeable substance such that removal of water vapor and other fluids from the leaf adhesion site of the skin surrounding the urethral meatus can occur and maceration is avoided.

In some preferred embodiments of the invention, the leaf comprises an adhesive substance and is provided with a vapor-permeable adhesive layer on the interior surface of each leaf, such that each leaf can be secured on the para-meatal surface.

To satisfy additional objects of the invention, there has been provided an external incontinence device comprising a housing which presents an outer surface and an inner surface wherein the inner surface, when positioned in approximation to a para-meatal surface, forms a cavity for receiving an adhesive compound. The housing comprises an injection port for receiving the adhesive compound into the cavity, the port penetrating through the housing into the cavity, and the housing comprising an outlet conduit for the drainage of urine and other physiological fluids, and the outlet conduit having an internal end and an external end, the internal end penetrating through the inner surface, wherein the internal end of the outlet conduit does not extend beyond the longest reach of the housing. For injection into the cavity, an adhesive compound is provided to hold the internal end of the outlet conduit in free communication with a urethral meatus.

In preferred embodiments of these "formed-in-place" configurations of the invention, the adhesive compound provided is permeable to physiological fluids and comprises a medically active substance which prevents microbial infiltration into the urethra.

In accordance with yet other objects of the invention, additional holding means of the device comprise a plurality of adhesive leaves equipped with U-shaped release backings which communicate with the vapor permeable adhesive on the leaves, such that the leaves are capable of wrinkle-free application to the para-meatal surface, and appropriate location and secure attachment of the device is maintained. The release backings of the inventions comprise a protective carrier portion which communicates with the vapor permeable adhesive layer and a pull tab which communicates with the carrier portion and extends away from the interior surfaces of the leaf, such that the application of force to the pull tab in a direction away from the housing causes a smooth transverse removal of the carrier portion from the leaf, whereby the leaf is applied to the para-meatal surface in a wrinkle-free manner.

In accordance with still other objects of the invention, in preferred female-adapted embodiments, the holding means further comprises a nonadhesive means for attaching the device to the para-meatal surface which is a plurality of retaining straps connected to a plurality of attachment points on the housing wherein the retaining straps are provided with a plurality of adjustment buckles for changing the length and fit of the retaining straps to further assure the maintenance of the device in the proper position with respect to the urethral meatus.

To satisfy yet additional objects of the invention, the fluid-absorptive material of the leaves comprises one or more substances from the group comprising hydrocolloids and polymer blends.

In accordance with additional objects of the invention, another means is provided for holding the housing in close approximation to the urethral meatus comprising an inner hollow, disposed on the inner surface of the housing, the hollow being suitable for receipt of an adhesive composition, and an adhesive composition suitable for deposit into said hollow. In preferred embodiments, the adhesive composition comprises an adhesive disc, an adhesive pad or a viscous liquid for adhering and sealing the device to a para-meatal surface.

In order to satisfy still other objects of the invention, an adhesive formulation suitable for making a barrier disc, an adhesive pad or wound treatment pad, is provided. A preferred formulation comprises 35–60% polyisobutylene, 10–20% sodium alginate, 10–20% pectin, 5–10% gelatin, 1–2% calcium silicate, 5–10% carboxymethyl cellulose and cellulosic derivatives and gums, 0.5–2% calcium chloride, 0.5–2% calcium phosphate, 0.5–2% calcium sulphate and 0.1–0.5% magnesium borate.

Another formulation suitable for making a barrier disc, an adhesive pad or wound treatment pad of the invention comprises 35–60% acrylic adhesive, 10–20% sodium alginate, 10–20% pectin, 5–10% gelatin, 1–2% calcium silicate, 5–10% carboxymethyl cellulose and cellulosic derivatives and gums, 0.5–2% calcium chloride, 0.5–2% calcium phosphate, 0.5–2% calcium sulphate and 0.1–0.5% magnesium borate.

Yet another formulation suitable for making a barrier disc, an adhesive pad or wound treatment pad of the invention comprises 15–30% acrylic adhesive, 15–30% polyisobutylene, 10–20% sodium alginate, 10–20% pectin, 5–10% gelatin, 1–2% calcium silicate, 5–10% carboxymethyl cellulose and cellulosic derivatives and gums, 0.5–2% calcium chloride, 0.5–2% calcium phosphate, 0.5–2% calcium sulphate and 0.1–0.5% magnesium borate.

To satisfy yet additional objects of the invention, is provided a two-component liquid adhesive, which is biocompatible and cures to a firm, flexible solid, the adhesive being suitable for adhering medical devices to skin. The adhesive comprises Component A and Component B, wherein Component A comprises 45–80% sodium alginate, 5–25% pectin, 5–25% carboxymethyl cellulose or cellulosic derivatives, and 1–5% gelatin, and has a viscosity in the range of 85–115 poise in aqueous solution; and wherein Component B is an emulsion which comprises 92–97% low molecular weight liquid acrylic adhesive or low molecular weight polyisobutylene, 1–3% calcium sulphate, 1.0–1.5% calcium chloride, 1–3% calcium silicate, 1.0–1.5% calcium phosphate and 1.0–1.5% magnesium borate. In preferred formulations of the two-component adhesive, the cellulosic derivatives are one or more from the group comprising carbopol, guar gum, gum acacia and gum tragacanth.

Another preferred formulation of the two-component adhesive is disclosed wherein Component A comprises 5–20% sodium alginate, and 80–95% low molecular weight acrylic adhesive or low molecular weight polyisobutylene, and Component B comprises 1.0–2.5% calcium sulphate, 1.0–2.5% calcium chloride, 1.0–2.5% calcium silicate, 1.0–2.5% calcium phosphate, 1.0–2.5% magnesium borate, 20–50% pectin, 10–20% gelatin, and 20–50% cellulosic derivatives.

Other objects, features and advantages of the present invention will become apparent from the following detailed description. It should be understood, however, that the detailed description and the specific examples, while indicating preferred embodiments of the invention, are given by way of illustration only. The detailed description herein will suggest changes and modifications within the spirit and scope of the invention that may become apparent to those skilled in the art. These changes and modifications are considered within the scope of the subject invention.

BRIEF DESCRIPTION OF THE DRAWINGS

In order that the invention may be more readily understood, and so that further features thereof may be appreciated, the invention will now be described by way of example with reference to the accompanying drawings, in which FIGS. 1–13 relate to eleven different embodiments of the external incontinence device of the invention and one embodiment of a storage/mixing container for use with some of the adhesive compositions of the invention and in which.

In describing the various embodiments of the incontinence device of the invention, the term "internal" means disposed toward a urethral meatus or penile skin surface and the term "external" means disposed away from a urethral meatus or penile skin surface. For example, the internal end of the conduit of the device is that end which is adapted for attaching to a para-meatal surface. Correspondingly the external end of the conduit is that end disposed away from the internal end.

DETAILED DESCRIPTION OF THE PREFERRED EMBODIMENTS

The present invention uses one or more adhesive means for attaching to a patient's para-meatal skin an anatomically contoured housing having an outlet conduit. The outlet conduit, which carries urine and other fluids away from the genital area, does not enter the body by extending beyond the urethral meatus but instead is held in close approximation to the urethral meatus by the device's adhesive means.

Several types of biocompatible adhesive ("bioadhesive") means are provided, such as leaves of a fluid-absorptive material which is itself inherently adhesive, or which is coated with an adhesive. Other means include leaves of vapor-permeable film or fluid-permeable compositions coated with a vapor-permeable adhesive, adhesive fluids injectable into a cavity or hollow of the housing, and an adhesive barrier disc or pad disposed around the urethral meatus to occlude microbes and other contaminants.

The urethral meatus is the external opening of the urethra in a male or female patient. In the male, the urethral meatus is typically found at the end of the penis. In the female, the urethral meatus is typically found anterior to the vaginal introitus (opening). The para-meatal surface is that surface which comprises the urethral meatus and surrounding skin or mucosal tissue near the urethral meatus in either the male or the female.

The leaf elements of the various embodiments of the invention can be provided with a vapor permeable adhesive. For example, an acrylic medical skin adhesive which is known in the art can be applied, in a continuous or discontinuous layer, on their interior surface. The adhesive or interior surface of the leaves attaches to the surface of the skin.

The vapor-permeable leaves preferably are comprised of 0.3 to 2.0 mil polyurethane film. The thinness and polymeric structure of the film allow moisture to escape from the skin surface through the leaves, thus maintaining a dry epidermal layer and reducing or eliminating skin irritation and maceration noted with the use of condom catheters and other conventional incontinence devices.

In some preferred embodiments of the invention, the leaves comprise a fluid-absorptive material, such as that comprising polymer blends and shown in Kashdan, U.S. Pat. No. 4,795,641. Materials of this type can be easily formed into sheets or films which are easily cut or stamped into leaves for attachment to housings of the invention.

Leaves of the invention are preferably provided in tapered shapes. The tapered shape of the leaves minimizes the area covered by the film while providing stable immobilization of the device. The tapered shape of the leaves also optimizes a smooth and wrinkle-free skin attachment of thin film leaves to a skin surface. In accordance with some preferred embodiments of the present invention, the leaves overlap at the housing and become gradually narrower as they proceed away from the housing, that is, the leaves are tapered. The leaves are wider and overlapping at the housing attachment site because secure attachment around the housing is critical. Therefore, through the use of vapor permeable film leaves with a skin compatible vapor permeable adhesive and a smaller surface area than that covered by conventional condom catheters, the present invention eliminates the skin irritation and maceration caused by condom catheters, diapers and incontinence pads.

The maceration and skin irritation associated with conventional condom catheters and other devices make the devices physically uncomfortable. By reducing maceration and skin irritation, patient comfort is increased, and patient compliance increases correspondingly. In addition, the present invention reduces or eliminates the incidence of infection from condom catheter use by reducing the opportunity for microbial infiltration of the urethral meatus.

A barrier disk layer is provided on the skin application surface of the housing. In a preferred embodiment of the present invention, the barrier disc layer includes an adhesive, for example, a hydrocolloid, to help hold the housing in close approximation to the urethral meatus. The barrier disc functions as a mechanically occlusive microbial-barrier layer, and in addition can contain either an antiseptic agent, such as povidone iodine or benzalkonium chloride, or an antimicrobial agent to inhibit bacterial growth. A preferred hydrocolloid is composed of a synthetic polyisobutylene adhesive (e.g. Vistanex®, Exxon Corp) 70%, pectin (e.g. Benecel®, Hercules Chemical, Inc.) 20% and povidone iodine (Betadine®, Purdue-Frederick, Inc.) 10%.

The barrier disc, when comprised of a hydrocolloid or an antiseptic material, can provide several infection control and skin protective advantages over other incontinence devices. The hydrocolloid disc forms an occlusive seal or mechanical barrier around the urethral meatus, thus protecting the entrance of the urinary tract from exposure to extraneous bacteria. The occlusive nature of the disc also prevents exposure of the para-meatal skin surface to the macerating effects of excreted urine. The hydrocolloid disc functions as an effective moisture barrier and seal. The excreted urine passes through the central opening of the disc, into the device housing and thence into an attached urinary drainage tube. Therefore, the remainder of the para-meatal surface is never exposed to the excreted urine, in distinction to condom catheters.

The barrier disc is preferably made of a hydrocolloid which absorbs skin perspiration and prevents accumulation of excess moisture on the skin surface. Therefore, the barrier disc helps to prevent maceration and skin irritation, as well as helps to oppose microbial infiltration.

The adhesive coated, vapor permeable leaves are made of a conformable film, enabling the leaves to assume the shape of the underlying para-meatal skin surface. The leaves are applied to the skin surface through removal of a novel U-shaped release backing on each leaf. These U-shaped release backings protect the vapor-permeable adhesive prior to application of the device. The U-shaped release backing allows each leaf to be applied to the skin surface in a wrinkle-free manner, from a point most proximal to the plastic housing to a point more distal from the plastic housing, with the device already in place on the para-meatal surface.

With respect to the release backing and pull tab components of the invention, "U-shaped" means that the pull tab is substantially parallel to the corresponding release backing and the two are connected at ends by an adhesive or by a weld so that the pull tab and the release backing approximate the arms of the letter "U" with the bottom of the "U" being the connection of the two pieces. This connection is of relatively small dimension when compared to the lengths of the pull tab and backing so that the arms of the "U" are relatively long. Alternatively, the pull tab and release backing can be one piece of material folded back on itself to also form, substantially, a "U" shape with the fold therein being the bottom of the "U".

The U-shaped release backing preferably is made of a thin plastic film, a piece of plastic or plastic-coated paper which is folded approximately in halves. One portion of the backing, the release portion, is located over the adhesive on the leaves, such that the adhesive layer is enclosed between the backing and the interior surface of the leaf. The other portion of the backing is folded back away from the leaf and comprises a pull tab. The pull tabs are of sufficient stiffness to provide that the application of force to each pull tab in a direction away from the housing causes a smooth transverse removal of the backing from the corresponding leaf. In a preferred embodiment, the pull tab portion of the backing has a greater modulus of rigidity than the release portion. The differential in rigidity facilitates the smooth and easy removal of the backing from the corresponding leaf. The pull tabs can be of various lengths, for example, in one preferred embodiment, the pull tab portion of the backing is longer than the release portion. The conformability of the leaf film and the design of the backings facilitate a smooth, wrinkle-free application of the leaves to the para-meatal surface. The resulting wrinkle-free layer of film on the skin surface ensures the maintenance of the proper location of the device proximate to the urethral meatus and a more secure adhesive attachment of the device. Moreover, the skin under the layer of film is protected from urine and other fluids.

The barrier disc creates a mechanical barrier to moisture and microbial infiltration because it provides an adhesive seal which is inherently occlusive. In a preferred embodiment, the barrier disc is made of a hydrocolloid with adhesive properties that adhere sufficiently strongly and intimately to the skin, that no additional attachment means are required. By protecting most of the penile surface from moisture exposure and microbial infiltration, the incidence of urinary tract infections, skin irritation and urine leakage associated with conventional condom catheter, invasive catheter, incontinence pad and diaper use are reduced or eliminated. An additional advantage of the invention is that it covers much less of a genital surface area than would be covered by other sheath-type devices.

Similar problems exist with respect to female incontinence. Due to a shorter urethra, female patients are particularly subjected to the infections associated with wearing invasive catheters, incontinence pads and diapers. Diapers and incontinence pads also cause skin irritation and maceration which potentially result in skin ulceration and infection, especially for bed-bound female patients.

The female-adapted urinary incontinence device functions in essentially the same way as the male-adapted device to solve these problems. The female-adapted device housing is contoured to accommodate the different shape of the female para-meatal surfaces and vaginal introitus. The barrier disc in the female-adapted device functions in the same way as it does in the male-adapted device, but it is also configured to conform to the female para-meatal surfaces and the vaginal introitus.

In one embodiment of the female device, additional nonadhesive attachment means are provided. In a preferred embodiment, the attachment means consists of several retaining straps attached to the exterior surface of the housing and to a retaining belt around the patient's waist. The retaining straps preferably have adjustment buckles to allow adjustment of the length of the retaining straps to fit differently sized patients.

Patients, male or female, can wear a device of the present invention for prolonged periods, for example, seven or more days. In contrast, the current condom catheter, diaper, and incontinence pad designs generally require that such devices be changed every day to reduce the risk of infection, skin maceration, irritation, urine leakage and to maintain an effective attachment. Presently, the cost of replacing conventional incontinence devices daily and the lack of properly supervised personnel in nursing homes and hospitals may result in these devices being worn longer than recommended by good medical practice. The risk of infection is thus increased. The ability to effectively wear the present invention for prolonged periods without infection will decrease the cost of treatment and reduce the personnel time required to change catheters or make diaper and bedding changes in long term care facilities.

The external incontinence device is applied to a patient's skin using aseptic technique and clean exam gloves. In a male patient, the foreskin is retracted and the urethral meatus, penile tip and corona are cleansed using gauze or cotton swabs moistened with a standard skin cleanser or antiseptic, such as povidone iodine or benzalkonium chloride. The penile tip is then thoroughly dried. A small amount of material to prepare the skin for adhesive attachment, such as tincture of Benzoin, may be applied to the penile tip surrounding the urethral meatus. This step facilitates improved adhesive attachment of the hydrocolloid disc and adhesive leaves to the penile tip. The protective release backing for the barrier disc is removed from the device and the housing is mounted on the penis with the outlet conduit centered over the urethral meatus. The U-shaped release backings are removed individually from each of the leaves by placing pressure on each leaf near the housing with one hand and pulling on the corresponding pull tab with the other hand, causing each leaf to adhere to the penis from the penile tip toward the corona and securing the device in place. The integral adaptor of the device housing is attached to an appropriate tubing connector, drain hose and urine collection assembly.

A similar attachment procedure is followed with respect to the female-adapted device except that the attachment leaves are applied as the labia minora surfaces are spread slightly to assure intimate contact of the adhesive surfaces with the para-meatal skin. In addition, in the preferred embodiment having attachment straps, the straps are adjusted to provide sufficient tension on the housing so that it remains in the desired position with respect to the urethral meatus.

The present invention can be more fully appreciated with reference to the above-noted figures depicting several embodiments of the invention and to the following detailed description of those figures. In connection with the foregoing figures, like reference numerals will refer to like portions thereof.

Although FIGS. 4–9, 11 and 12 depict male-adapted forms of the invention, it can easily be understood that female adaptations of the several devices can be created with only minor modifications to the male-adapted forms. The embodiments of the invention shown in FIGS. 1–3, and 10 are particularly suitable for use on either males or females.

All of the devices of the invention are suitable for attachment to tubing, receptacles, withdrawal syringes or other apparatus useful for draining away urine and other fluids from genital surfaces. For example, the external end of the conduit of the invention may be adapted to fit various medical tubing and device connectors, such as standard barbed "Christmas Tree" tubing connectors, or luer fittings.

Figure 1:
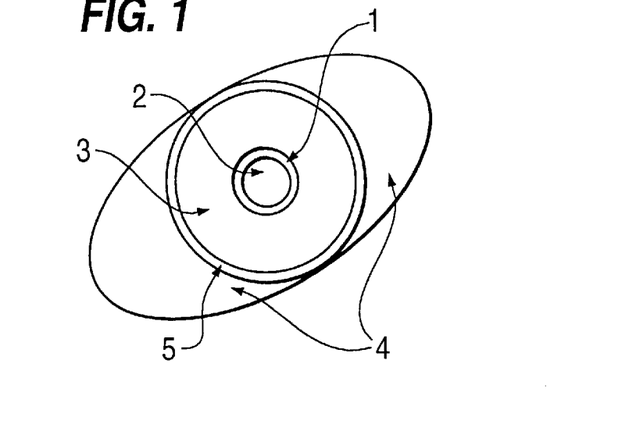
FIG. 1 is an attachment surface view of the internal end of a male-adapted external incontinence device with two attachment leaves.

FIG. 1 is an attachment surface view of the internal end of a male-adapted external incontinence device with two attachment leaves. Annular barrier disc 3 is shown disposed on the inner surface of housing 9 (not shown) formed of plastic or of other moldable, castable or machinable material. Barrier disc 3 is surrounded by tapered lip 5 of housing 9 and is penetrated by the internal end of outlet conduit 2 which has meatal approximation ring 1 formed at the internal end of outlet conduit 2. When the device is in use, the longitudinal axis of outlet conduit 2 and the opening of barrier disc 3 are aligned with the longitudinal axis of a urethra (not shown) to thereby provide an unbroken channel for the drainage of urine and other fluids away from the genital area. Meatal approximation ring 1 provides alignment guidance when attaching the device. Barrier disc 3, which is formed of an adhesive composition or is provided with an adhesive layer, provides adhesive attachment sufficient to hold the device in place on the end of a penis (not shown). Additional attachment force is provided by the two leaves 4 which adhere to the para-meatal surface of the penis by means of a vapor permeable adhesive (not shown) on their skin attachment surface.

Figure 2:
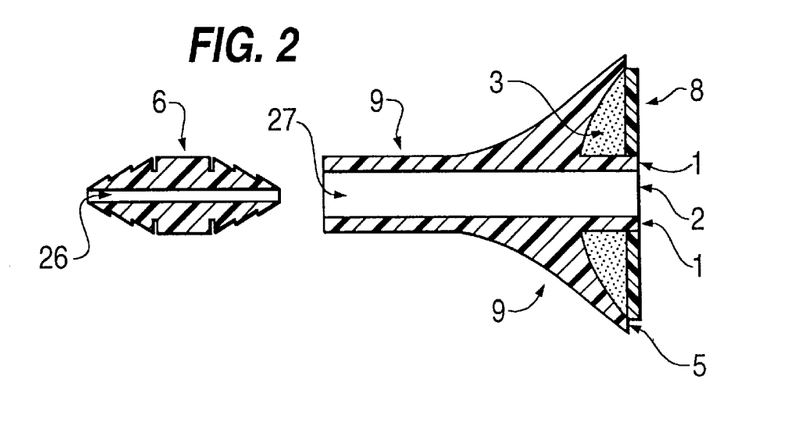
FIG. 2 is a cross-sectional view of a male-adapted device having a barrier disc and no leaves.

FIG. 2 is a cross-sectional view of a male-adapted device having a barrier disc and no leaves. Protective release backing 8 adheres releasably to barrier disc 3 and is removed from disc 3 immediately prior to placement of the disc on a para-meatal genital surface. Barrier disc 3 is surrounded by tapered lip 5 of plastic housing 9 and is penetrated by the internal end of outlet conduit 2 which has meatal approximation ring 1 formed at the internal end of outlet conduit 2. Barrier disc 3, which is formed of an adhesive composition or is provided with an adhesive layer, provides adhesive attachment to hold the device in place over the end of a penis (not shown). When attaching the device to a penis (not shown), meatal approximation ring 1 aligns with the walls of the dorsal slit of the penis and is thereby used to align the axis of the conduit with that of the urethra. FIG. 2 also shows tubing connector 6, a standard barbed "Christmas Tree" connector well known in the medical field. Tubing connector 6 has channel 26 therethrough and is shown aligned for insertion into the external end 27 of outlet conduit 2 formed in housing 9.

Figure 3:
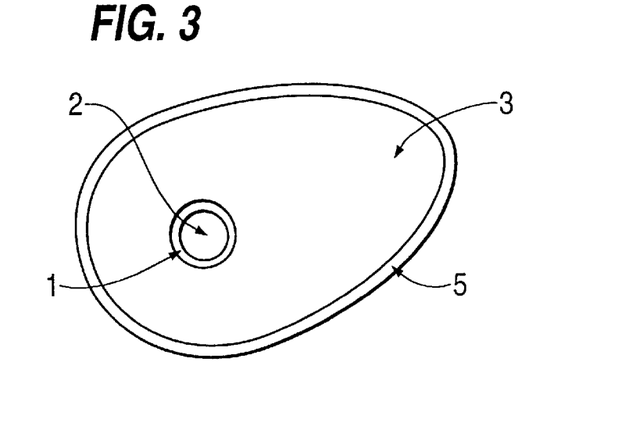
FIG. 3 is an attachment surface view of the internal end of an embodiment of the device having an elongated barrier disc which comprises an integral leaf-type attachment surface.

FIG. 3 is an attachment surface view of the internal end of an embodiment of a female-adapted device having an elongated barrier disc 3, wherein the integral elongated portion of barrier disc 3 functions as an adhesive leaf. The elongated portion is shaped to attach to the para-meatal surface of an anterior vaginal wall so that the meatal approximation ring 1 of outlet conduit 2 closely approximates the urethral meatus. Barrier disc 3 is shown disposed on the inner surface of the housing surrounding the outlet conduit 2 and meatal approximation ring 1 of the housing. Barrier disc 3, which is formed of an adhesive composition or is provided with an adhesive layer, provides adhesive attachment to hold the device in place at the vaginal introitus.

Figure 4:
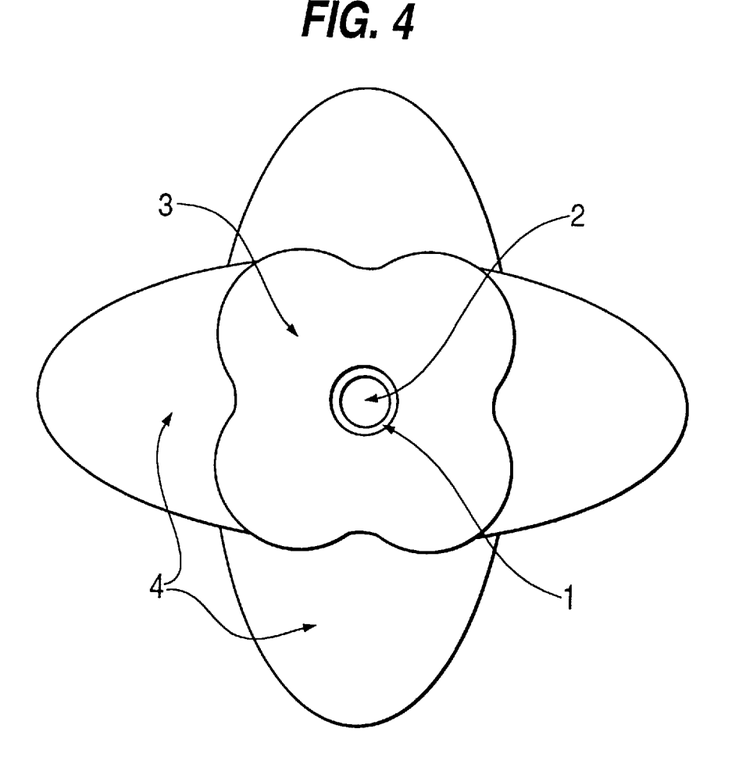
FIG. 4 is an attachment surface view of the internal end of an embodiment of a male-adapted device having four attachment leaves.

FIG. 4 shows an attachment surface view of the internal end of a preferred embodiment of the device having four vapor-permeable attachment leaves. Four-lobed barrier disc 3 is shown disposed on the inner surface of the housing and surrounding outlet conduit 2 and meatal approximation ring 1 of the housing. In use, barrier disc 3 attaches on the end of a penis (not shown) with the meatal approximation ring 1 closely approximating the urethral meatus. Barrier disc 3, which is formed of an adhesive composition or is provided with an adhesive layer, provides adhesive attachment to hold the device in place over the end of a penis (not shown). Additional adhesive attachment is provided by the four leaves 4 which adhere to the para-meatal surface of the penis by means of a vapor permeable adhesive (not shown) on their skin attachment surfaces.

Figure 5:
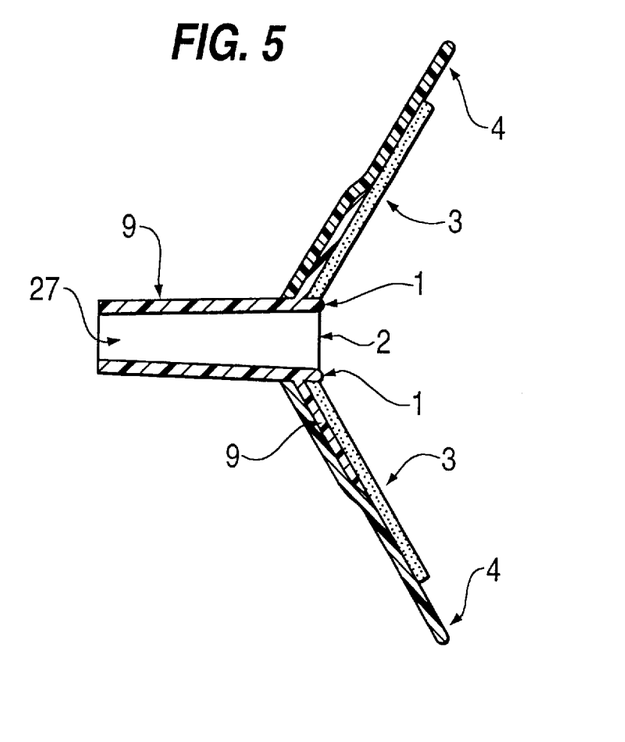
FIG. 5 is a cross-sectional side view of an embodiment of the device having a barrier disc internal to and overlaid by attachment leaves.

FIG. 5 is a cross-sectional side view of a preferred embodiment of the invention having barrier disc 3 internal to and overlaid by attachment leaves 4. Adhesive attachment leaves 4 are attached firmly to housing 9 and extend beyond the farthest reaches of barrier disc 3. Leaves 4 are provided with a vapor permeable adhesive (not shown) and are disposed to adhere to the para-meatal surface of a penis (not shown) to hold the device in position on the glans. Barrier disc 3, which is formed of an adhesive composition or is provided with an adhesive layer, provides additional adhesive attachment to that of the attachment leaves to hold the device in place on the end of a penis and to hold the internal end of outlet conduit 2 in sealed alignment and free communication with a urethra. Outlet conduit 2 has external end 27 formed in housing 9 and adapted for attachment to a standard medical tubing connector.

Figure 6:
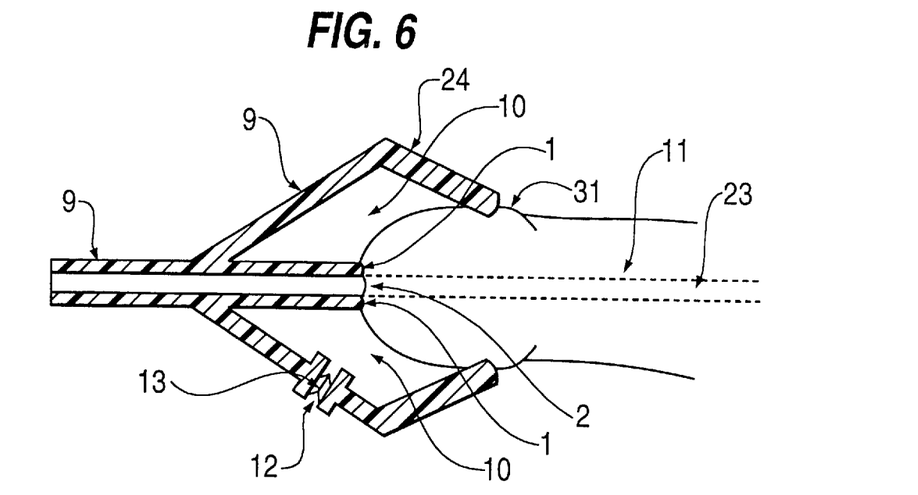
FIG. 6 is a cross-sectional side view of an embodiment of the device in use on a penis and forming a cavity for receipt of a fluid adhesive compound.

FIG. 6 is a cross-sectional side view of a preferred embodiment of the invention having a cavity 10 for receipt of a fluid adhesive compound. The device is shown in contact with a penis 11 (also shown in cross-section) having urethra 23. Meatal approximation ring 1 is shown in close contact with the para-meatal skin of urethra 23 of penis 11 so that internal end of outlet conduit 2 communicates freely with urethra 23. Corona engagement cone 24 is shown in contact with the skin adjacent to penile corona 31. In the position shown, the device is ready to receive an injectable fluid adhesive into cavity 10. To attach the device to a penis, a fluid adhesive is injected through injection port 12 having valve 13 to charge cavity 10. The fluid adhesive sets quickly into a solid or semi-solid to thereby secure the device to the skin and to seal the internal end of outlet conduit 2 in close approximation to the urethral meatus of the penis 11. Thus secured, the device permits the free flow of urine and other fluids through outlet conduit 2 and away from penis 11.

Figure 7:
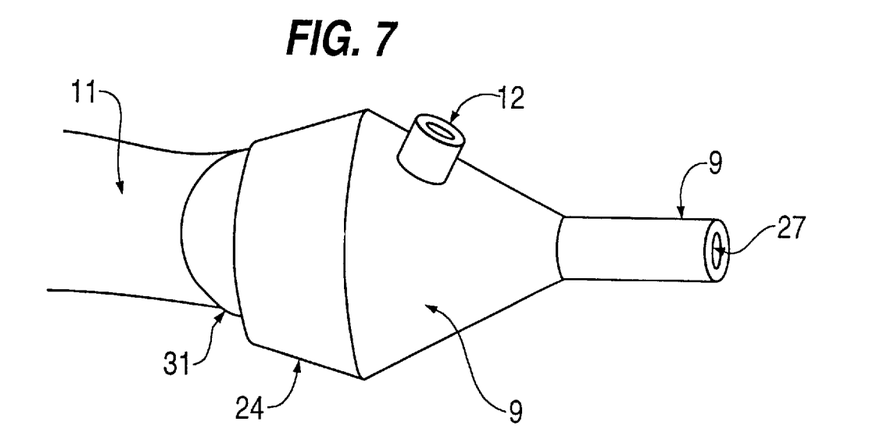
FIG. 7 is a side view of the exterior of the mold-in-place adhesive embodiment of the device shown in cross-section in FIG. 6 depicting the chamber for receiving an adhesive.

FIG. 7 is a side view of the exterior of the mold-in-place adhesive embodiment of the device shown in cross-section in FIG. 6 depicting the chamber for receiving an adhesive. The invention is shown attached securely to penis 11 by means of a charge of fluid adhesive injected into and solidified within cavity 10 (shown in FIG. 6) formed by the inner surface of housing 9 and the para-meatal surfaces of penis 11. Corona engagement cone 24 is shown in contact with the skin adjacent to the penile corona 31. Injection port 12 permits a charge of fluid adhesive to be injected into and solidified within cavity 10 (shown in FIG. 6). When the device is adhered in place as shown, the free flow of urine and other fluids through the outlet conduit and away from penis 11 is permitted.

Figure 8:
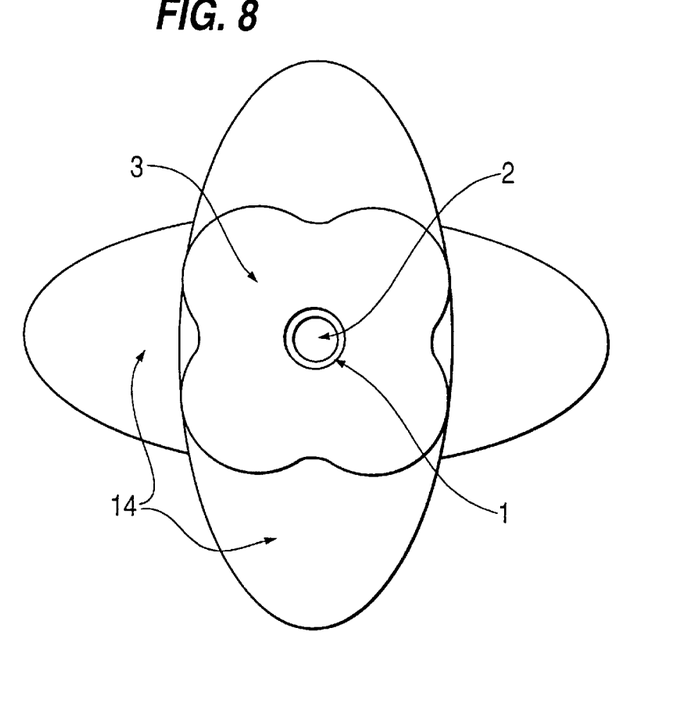
FIG. 8 is an attachment surface view of the internal end of an embodiment of a male-adapted device having four attachment leaves comprising hydrophilic foam.

FIG. 8 is an attachment surface view of the internal end of an embodiment of a male-adapted device having four attachment leaves 14 comprising hydrophilic form for example of the polymer blend type as shown in U.S. Pat. No. 4,795,641 to Kashdan. Four-lobed barrier disc 3 is shown disposed on the inner surface of the housing and surrounding outlet conduit 2 and meatal approximation ring 1 of the housing. In use, barrier disc 3 attaches on the end of a penis (not shown) with the meatal approximation ring 1 closely approximating the urethral meatus. Barrier disc 3, which is formed of an adhesive composition or is provided with an adhesive layer, provides adhesive attachment to hold the device in place on the end of a penis (not shown). Additional adhesive attachment is provided by the four hydrophilic leaves 14 which adhere to the para-meatal surface of the penis by means of a vapor permeable adhesive (not shown) on their skin attachment surfaces.

Figure 9:
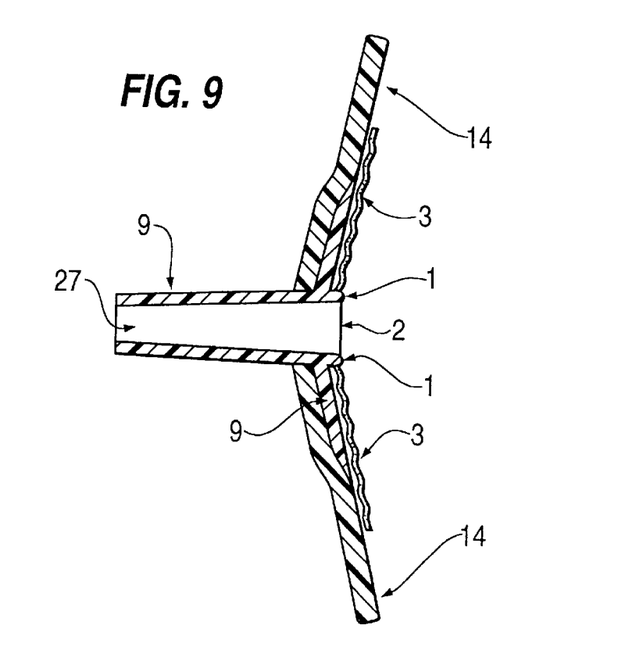
FIG. 9 is a cross-sectional side view of an embodiment of the device having a barrier disc internal to and overlaid by hydrophilic attachment leaves.

FIG. 9 is a cross-sectional side view of an embodiment of the device having a barrier disc internal to and overlaid by hydrophilic attachment leaves which absorb urine and other fluids from the attachment surfaces to thereby remove them from the surfaces and avoid skin maceration. Hydrophilic attachment leaves 14 are attached firmly to housing 9 and extend beyond the farthest reaches of barrier disc 3. Leaves 14 are provided with a vapor permeable adhesive (not shown) on their skin attachment surfaces and are disposed to adhere to the para-meatal surface of a penis (not shown) to hold the device in position on a genital surface. Barrier disc 3, which is formed of an adhesive composition or is provided with an adhesive layer, provides adhesive additional attachment to that of the attachment leaves to hold the device in place on the end of a penis and to hold the internal end of outlet conduit 2 in sealed alignment and free communication with the urethral meatus. Outlet conduit 2 has external end 27 formed in housing 9 and adapted for attachment to a standard medical tubing connector.

Figure 10:
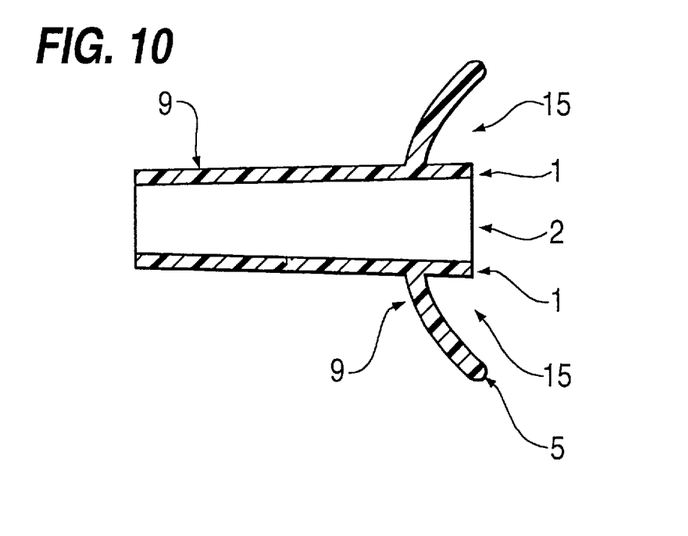
FIG. 10 is a cross-sectional side view of an embodiment of the device having a hollow for receipt of an adhesive composition or pad for adhering the device to a para-meatal surface.

FIG. 10 is a cross-sectional side view of a preferred embodiment of the device having an inner hollow 15 for receipt of an adhesive composition, adhesive disc or adhesive pad for adhering and sealing the device to a para-meatal surface. Prior to attaching the device to a para-meatal surface, an adhesive composition, such as a viscous fluid hydrocolloid gel (not shown), adhesive annular barrier disc (not shown), or annular adhesive pad (not shown), is deposited into inner hollow 15 formed by the inner surface of housing 9 and extending to lip 5 of housing 9. Inner hollow 15 is breached by the internal end of outlet conduit 2 which has meatal approximation ring 1 formed therein. To attach the device to a para-meatal surface, the gel, disc or pad is deposited into hollow 15 to adhere to housing 9 and to surround the internal end of outlet conduit 2. The device is then placed with meatal approximation ring 1 in close approximation to the urethra meatus. The gel, disc or pad adhere to hollow 15 and to the para-meatal surface to adhere the device in place. Thus adhered, the device permits the free flow of urine directly from the urethral meatus (not shown) through outlet conduit 2 and away from genital surfaces.

Figure 11:
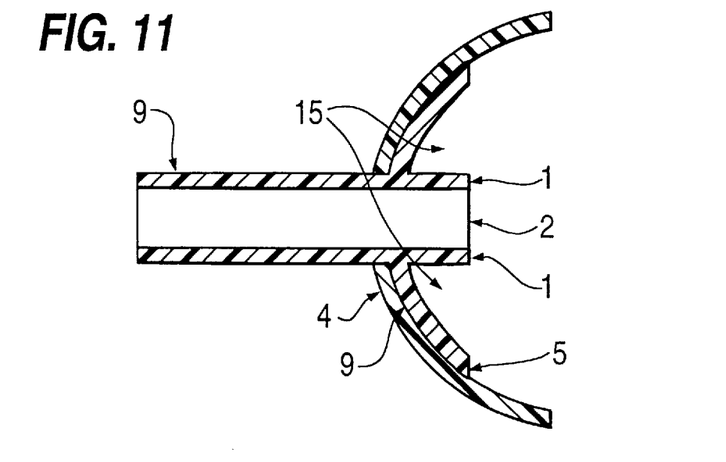
FIG. 11 is a cross-sectional side view of an embodiment of the device having vapor-permeable leaves and a hollow for receipt of a barrier disc or adhesive structure.

FIG. 11 is a cross-sectional side view of an embodiment of the device having vapor-permeable leaves and a hollow for receipt of a barrier disc or adhesive structure. Vapor-permeable film leaves 4, which are firmly attached to housing 9 by an adhesive, adhere to the para-meatal surface of a penis to provide adhesive attachment in addition to that provided by a viscous fluid hydrocolloid gel (not shown), adhesive annular barrier disc (not shown), or annular adhesive pad (not shown), deposited into inner hollow 15. Leaves 4 are provided with a vapor-permeable adhesive (not shown) on their skin attachment surfaces.

Figure 12:
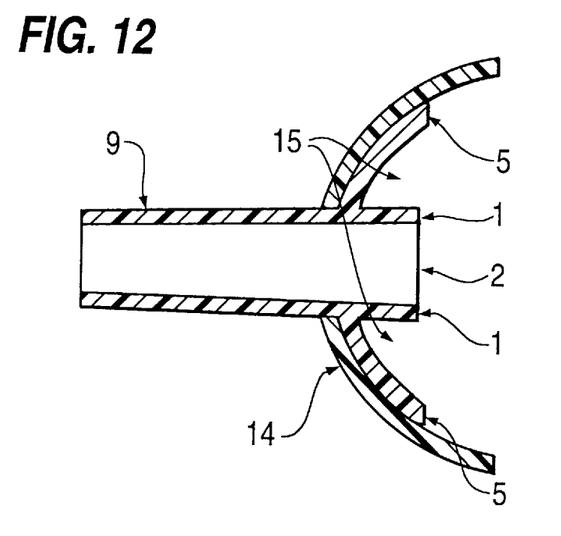
FIG. 12 is a cross-sectional side view of an embodiment of the device having hydrophilic foam leaves and a hollow for receipt of a barrier disc or adhesive structure.

FIG. 12 is a cross-sectional side view of an embodiment of the device having hydrophilic foam leaves and a hollow for receipt of a barrier disc or adhesive structure. Vapor-absorptive leaves 14, which are firmly attached to housing 9 by an adhesive, adhere to the para-meatal surface of a penis to provide adhesive attachment in addition to that provided by a viscous fluid hydrocolloid gel (not shown), adhesive annular barrier disc (not shown), or annular adhesive pad (not shown), deposited into inner hollow 15. Leaves 14 are provided with a vapor-permeable adhesive (not shown) on their skin attachment surfaces.

Figure 13:
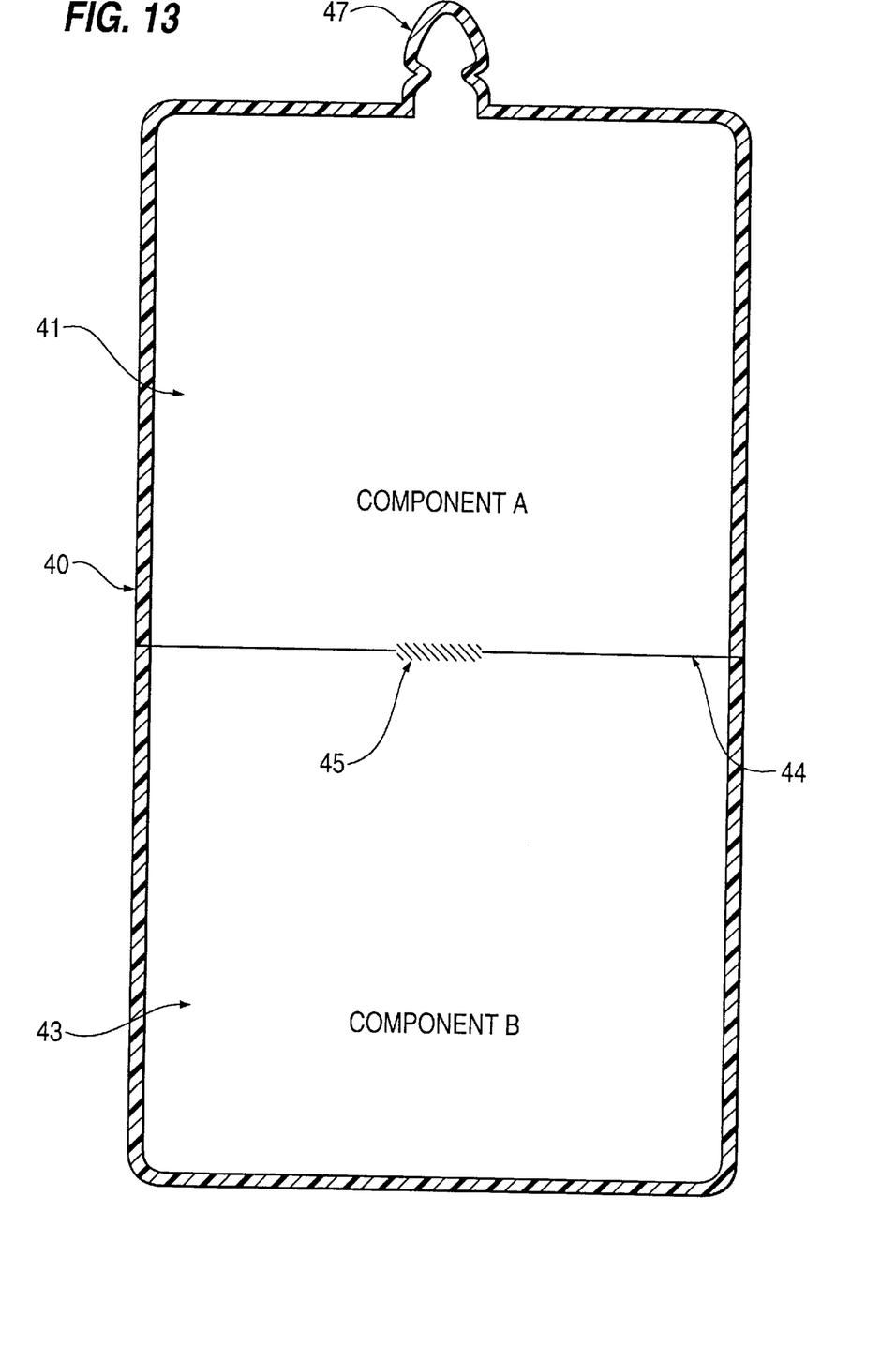
FIG. 13 is a cross-sectional side view of an embodiment of a storage/mixing container of the device suitable for storing and mixing the two-component adhesives of the invention.

FIG. 13 is a cross-sectional side view of an embodiment of a storage/mixing container of the device suitable for storing and mixing the two adhesive components of the two-component liquid adhesive of the invention. Components A and B are stored in chambers 41 and 43 of container 40 formed of a pliable material. Chambers 41 and 43 are separated by membrane 44 having breakaway septum 45 disposed therein. To formulate the adhesive immediately prior to use with an embodiment of the invention having an inner hollow for receipt of an adhesive, breakaway septum 45 is ruptured by squeezing container 40 to allow mixing of Components A and B. Container 40 is kneaded manually to mix the components thoroughly. The resultant viscous semi-liquid adhesive is thereafter expelled through tear-open nozzle 47 into the inner hollow 15 of housing 9 adapted for receipt of the adhesive.

One of skill in the medical arts would comprehend clearly that many other variations and permutations of the invention are possible, other than those shown in the drawings. For instance, by substituting two fluid-absorptive leaves for two of the vapor-permeable leaves shown in FIG. 4, yet another embodiment of the invention is obtained.

One of skill in the medical arts would comprehend also that many other configurations of the housing element of the device, other than those shown in the drawings, are within the spirit of the invention. Thus, by varying the length and diameter of the internal end of the outlet conduit, or the shape of the alignment ring, a variety of devices can be adapted to conform to any genital para-meatal surface. It is also clear that the inner surface of the housing can be sized and shaped to conform to any genital para-meatal surface.

With the exception of the barrier disc, the elements of the present invention are manufactured by standard manufacturing procedures and from materials well-known in medical device manufacturing. The housing, leaves and barrier disc of the invention can be manufactured by standard manufacturing procedures well-known in the medical device manufacturing art. For example, in one preferred embodiment of the invention, the housing is injection molded using a soft, pliable grade of polyurethane (i.e., Kraton G, available from Shell Plastics Company), the leaves are die-cut from 1.0 mil vapor-permeable polyurethane film, previously coated with 1.0 mil of acrylic bio-compatible porous adhesive (available from Semex of Malvern, Pa.), and the barrier disc is die-cut from an extruded sheet compounded in accordance with one of the disclosed hydrocolloid compositions of the invention described herein. Any required U-shaped release backings are applied in a secondary converting step prior to final die-cutting.

Although any hydrocolloid having strong adhesive properties and compatibility with both skin and plastic is suitable for use as a barrier disc, adhesive pad or wound treatment pad in the invention, preferred compositions comprise components from five groups of materials known in the medical field. The five groups are:

(1) adhesive bases
(2) gelling agents
(3) absorptive agents
(4) setting agents; and
(5) anti-microbial agents The following examples of ingredients included in groups 1–5 are illustrative and not exclusive. Although the combinations of the ingredients yield novel medical formulations, the ingredients themselves are known, or of a type known, in the art.

Adhesive bases of the compositions of the invention include polyisobutylenes and acrylics, both of which possess the desirable characteristics of biocompatibility and strong adhesiveness for skin and plastics. Other suitable adhesive bases include any of the non-toxic polymers, particularly those of the type known in the medical arts including natural or synthetic elastomers, such as styrene, butadiene, styrene isoprene block copolymers, urethanes, silicones, styrene butadiene copolymers, methyl acrylate copolymers, acrylic acid, polyacrylates, Particularly preferred bases are bioadhesives for application to the epithelium, preferably compatible with mucosal surfaces and exposed dermis. When a polyisobutylene (PIB) is used, the preferred type is a hot-melt, solvent-free compound with a high molecular weight ("MW"). An example of an acceptable high MW polyisobutylene is Vistanex® L-140 available from Exxon Corp. and having a MW in the range of from 117,000 to 135,000 daltons. Other preferred embodiments of the invention may employ low MW polyisobutylenes such as Vistanex® LMH with a MW in the range of from 11,600 to 12,300 daltons. In other preferred embodiments, a high MW acrylic adhesive may ne specified such as HRJ-4326 with a MW in the range of 105,000 to 125,00 daltons, available from Schenectedy International, Inc., of Schenectedy, N.Y. Still other preferred embodiments may require lower MW acrylic adhesives such as HRJ-10753 with a MW in the range of 81,000–91,000 daltons, also available from Schenectedy International, Inc., of Schenectedy, N.Y. In a typical composition of the invention, the adhesive base comprises 20–60 wt. % of the total.

The term "adhesive" as used herein means a substance, inorganic or organic, natural or synthetic, that is capable of surface attachment to the intended application site of the skin or device.

The term "bioadhesive" as used herein means an adhesive which attaches and preferably strongly attaches to a biological surface such as skin or mucosal tissue. Preferable bioadhesives, are substances which are capable of maintaining adhesion in moist or wet in vivo or in vitro environments. Some of the compositions of the present invention are "self-adhesive" in that they attach to the device and body site of interest without the need to reinforce their attachment by way of another adhesive which is applied to an attachment surface or by way of adhesives applied to additional attachment surfaces such as leaves.

In formulating adhesive compounds to be used with the various embodiments of the invention, the strength of adherence of a particular compound to a surface can be measured by standard tests for measuring the force, e.g. in dynes per square centimeter, as disclosed in U.S. Pat. No. 4,615,697.

For the purpose of the subject invention, gel agents are biocompatible compounds which, when exposed to water or aqueous solutions, form a solid gel, gelatin or highly viscous liquid. Gel Agents of the formulations of the invention include sodium alginate, pectin, gelatin and agar. These gel agents are readily available from suppliers of medical or pharmaceutical components.

Absorptive agents useful in the compositions of the invention include calcium silicate, and natural or synthetic polysaccharides. The term "polysaccharide" as used herein means a carbohydrate decomposable by hydrolysis into two or more molecules of monosaccharides or their derivatives. Suitable polysaccharides include cellulose derivatives such as methylcellulose, cellulose acetate, carboxymethylcellulose, hydroxyethylcellulose and the like.

Certain absorptive agents possess the capability to absorb and hold water or aqueous fluids in a colloidal mass. In a typical hydrated colloidal mass, the absorbed water or aqueous fluid may weigh many times the weight of the absorptive agent. These absorptive agents include polysaccharides such as, karaya gum, tragacanth gum, pectin, guar gum, cellulose, and cellulose derivatives such as methyl cellulose, propyl cellulose, cellulose acetate and the like, along with other substances known for use in forming a solid colloid that can adhere to skin and mucosa, used alone or in combination with various adhesive bases.

Other suitable absorptive agents include those prepared optionally from partially esterified polyacrylic acid polymers, including but not limited to, polyacrylic acid polymers lightly crosslinked with a polyalkenyl polyether such as those commercially available from B. F. Goodrich, Cincinnati, Ohio, under the trademarks Carbopol 934, 934P, 940 and 941.

Additional suitable absorptive agents include hydrophilic polysaccharide gums such as natural plant exudates, including karaya gum, ghatti gum, tragacanth gum, xanthan gum, jaraya gum and the like, as well as seed gums such as guar gum, locust bean gum, psillium seed gum and the like.

Setting agents suitable for the compositions include calcium salts such as calcium chloride, calcium phosphate and calcium sulphate. The corresponding magnesium salts may also be useful as setting agents.

Anti-microbial agents of the invention include the anti-fungal agent magnesium borate and other known topical anti-microbial agents, including bacitracin zinc, povidone iodine, benzalkonium chloride, neomycin sulfate, polymyxin B sulfate, silver sulfadiazine and mupirocin (available from Beecham, Inc. of Bristol, Tenn.).

The compositions of the invention are formed by mixing one or more components from each of Groups 1–5. Thus, it can be seen that numerous variations of the claimed compositions can be formulated from one or more adhesive bases, one or more gelling agents, one or more absorptive agents, and one or more setting agents. When sodium alginate is used as one of the gelling agents, a calcium salt such as one of the disclosed setting agents can be used to solidify a two-component liquid preparation or to improve the cohesiveness of a solid hydrocolloid. In general, each formulation will require at least 10% adhesive base to provide sufficient adhesive properties and at least 20% of combined absorptive and/or gel agents to provide sufficient hydrophilic characteristics.

In addition to the above ingredients, there may also be incorporated other additives selected from among the various medically acceptable additives available to those skilled in the art. These additives include binders, stabilizers, preservatives and pigments.

Exemplified below are formulations of a solid hydrocolloid useful for compounding a skin adhesive, barrier disc or wound care pad. Percentages of the ingredients are given in weight percent; for example, a formulation utilizing 60% of PIB would require 60 grams of PIB combined with 40 grams of the remaining four components to yield 100 grams of the formulation.

In one preferred embodiment, the solid hydrocolloid comprises 20–60% PIB, 10–20% sodium alginate, 10–20% pectin, 5–10% gelatin, 1–2% calcium silicate, 5–10% carboxymethyl cellulose and cellulosic derivatives and gums, 0.5–2% calcium chloride, 0.5–2% calcium phosphate, 0.5–2% calcium sulphate and 0.1–0.5% magnesium borate.

A second preferred embodiment of the solid hydrocolloid formulation of the invention comprises 20–60% acrylic adhesive, 10–20% sodium alginate, 10–20% pectin, 5–10% gelatin, 1–2% calcium silicate, 5–10% carboxymethyl cellulose and cellulosic derivatives and gums, 0.5–2% calcium chloride, 0.5–2% calcium phosphate, 0.5–2% calcium sulphate and 0.1–0.5% magnesium borate.

A third preferred embodiment of a solid hydrocolloid formulation of the invention comprises 10–30% acrylic adhesive, 10–30% PIB, 10–20% sodium alginate, 10–20% pectin, 5–10% gelatin, 1–2% calcium silicate, 5–10% carboxymethyl cellulose and cellulosic derivatives and gums, 0.5–2% calcium chloride, 0.5–2% calcium phosphate, 0.5–2% calcium sulphate and 0.1–0.5% magnesium borate.

In a fourth preferred embodiment, the solid hydrocolloid comprises 0–60% acrylic adhesive, 0–60% PIB, 10–20% sodium alginate, 10–20% pectin, 5–10% gelatin, 1–2% calcium silicate, 5–10% carboxymethyl cellulose and cellulosic derivatives and gums, 0.5–2% calcium chloride, 0.5–2% calcium phosphate, 0.5–2% calcium sulphate and 0.1–0.5% magnesium borate.

In a fifth preferred embodiment, the solid hydrocolloid comprises 25% acrylic adhesive, 25% PIB, 20% sodium alginate, 14% pectin, 4% gelatin, 1.75% calcium silicate, 5% carboxymethyl cellulose and cellulosic derivatives and gums, 2% calcium chloride, 2% calcium phosphate, 1% calcium sulphate and 0.25% magnesium borate.

In a sixth preferred embodiment, the solid hydrocolloid of the invention comprises 25% acrylic adhesive, 25% PIB, 10% sodium alginate, 10% pectin, 5% gelatin, 4% calcium silicate, 20% carboxymethyl cellulose and cellulosic derivatives and gums, 0.25% calcium chloride, 0.25% calcium phosphate, 0.25% calcium sulphate and 0.25% magnesium borate.

In a seventh preferred embodiment, the solid hydrocolloid comprises 0–60% acrylic adhesive, 0–60% PIB, 10–40% sodium alginate, 10–40% pectin, 1–2% calcium silicate, 0.5–2% calcium chloride, 0.5–2% calcium phosphate, 0.5–2% calcium sulphate and 0.0–0.5% magnesium borate.

In an eighth preferred embodiment, the solid hydrocolloid comprises 0–60% acrylic adhesive, 0–60% PIB, 10–40% sodium alginate, 0–20% pectin, 1–2% calcium silicate, 0.5–2% calcium chloride, 0.5–2% calcium phosphate, 0.0–40% gelatin, 0.5–2% calcium sulphate and 0.0–0.5% magnesium borate.

A fluid adhesive that cures to a firm, flexible solid material with excellent material cohesion and skin adhesion properties is required for use with embodiments the invention of the types shown in FIGS. 10 and 11. The preferred adhesives are rapid curing, organic solvent-free and are useful for binding many types of medical devices to skin and mucosal surfaces. The two components of the adhesive are mixed immediately prior to use as shown in FIG. 13 and the description above.

One example of a two-component adhesive formulation is that wherein Component A is an aqueous solution or suspension having total solutes or suspended particles that yield a viscosity in the range of 85 to 115 poise. The solids of Component A comprise at least 60% sodium alginate, 0.0–30% calcium-free carboxymethyl cellulose and/or cellulosic derivatives such as carbopol, guar gum, gum acacia and gum tragacanth. To combine with this specific Component A, Component B is an emulsion comprising 60–95.25% low molecular weight liquid acrylic adhesive or low molecular weight polyisobutylene, 1.0–10% calcium sulphate, 0.25–10% calcium chloride, 2% calcium silicate, 0.25–10% calcium phosphate and 0.0–0.5% magnesium borate; Component B may also comprise gelatin and pectin.

A second example of a two-component adhesive formulation is that wherein Component A comprises 60–95% low molecular weight acrylic adhesive or low molecular weight polyisobutylene having suspended or dissolved therein 5–40% sodium alginate; and wherein Component B comprises an aqueous solution or suspension having total solutes or suspended particles which yield a viscosity in the range of 75 to 125 poise, 0.1–10% calcium sulphate, 0.1–10% calcium chloride, 0.1–5% calcium silicate, 0.1–10% calcium phosphate, 0.0–0.5% magnesium borate, 2–40% pectin, 0.0–40% gelatin, and 0.0–35% cellulosic derivatives.

Injectable adhesive compositions for use with the embodiments of the invention requiring an injectable fluid adhesive, such as those shown in FIGS. 6 and 7, are disclosed by way of example. One preferred embodiment of an injectable hydrocolloid of the invention comprises 65% PIB adhesive, 20% pectin, 10% povidone iodine and 5% mineral oil. In a second preferred embodiment, the hydrocolloid comprises 55–75% PIB adhesive, 10–25% pectin, 0–20% povidone iodine and 0–10% mineral oil. In a third embodiment, the hydrocolloid comprises 20–30% polyisobutylene, 45–55% pectin, 10% povidone iodine and 5% mineral oil.

In a fourth preferred embodiment of an injectable fluid adhesive of the invention, the hydrocolloid comprises 45–75% polyisobutylene, 20–40% pectin, 5–15% povidone iodine and 4–10% mineral oil. In a fifth preferred embodiment of an injectable fluid adhesive, the formulation comprises 65% PIB adhesive, 28% pectin, 0.1–2.0% benzalkonium chloride and 5% mineral oil. A sixth preferred embodiment of an injectable fluid adhesive hydrocolloid comprises 55% polyisobutylene, 30% pectin, 0.1–2% benzalkonium chloride and 8–10% mineral oil. A seventh preferred embodiment of an injectable hydrocolloid comprises 45–60% PIB adhesive, 10–35% pectin, 0–5% benzalkonium chloride, 4–10% mineral oil, 0–25% gelatin, and 0–25% sodium alginate. An eighth preferred embodiment is a hydrocolloid comprising 20–30% PIB adhesive, 20–60% pectin, 0–5% benzalkonium chloride 5–10% mineral oil, and 0–20% sodium alginate.

Injectable adhesive foams also may be used to form the injectable adhesive component of the invention. In one preferred embodiment of an injectable adhesive component of the invention, the closed cell adhesive foam comprises 90–95 wt. % low molecular weight acrylic adhesive with a high degree of tack (i.e., HRJ 10753 from Schnectady International, Schnectady, N.Y.), 1–2% ultra-violet reactive monomer (i.e., trimethylol propane triacrylate), 1–2% photo-initiator (i.e., Darocur 1173, from CIBA), and 1–2% foaming/blowing agent (i.e., carbon dioxide).

From the foregoing description, it is evident that there are a number of changes, adaptations and modifications of the subject invention that are within the province of those persons having ordinary skill in the pertinent art. The inventor intends that all such variations, not departing from the spirit of the subject invention, be considered as within the scope of the subject invention as limited only by the appended claims.

For instance, the devices can also be used to seal occlusively catheters and other skin-breaching devices to skin. More specifically, the embodiments of the invention shown in FIGS. 1–5 and 8–12, can be used to sealably surround a skin entrance site for a wire or catheter. By threading a wire or catheter through conduit 2 of the invention, and by providing an antimicrobial/sealing composition to occlusively surround the wire or catheter in the conduit, an occlusive attachment of the wire or catheter to the skin is achieved.

The disclosed hydrocolloid compositions can also be used to produce wound dressings and as formulations for attaching other medical devices to skin. Wound dressings produced using the disclosed hydrocolloid compositions provide a variety of characteristics advantageous to wound care. Because of this, the hydrocolloids of the invention are particularly suited for production of moist and occlusive wound dressings, wound packing materials for decubitus ulcers, venous stasis ulcers, traumatic skin wounds and avulsions, ulcers due to vascular insufficiency, burns, and for dressings for split-thickness skin graft donor sites, surgical incisions, reconstruction or repairs, radiation dermatitis, and other dermatologic conditions or diseases that result in physiologically damaged or compromised skin or a loss of skin integrity, including macerated epidermis.

The hydrocolloid compositions of the invention can also be used to treat any condition that involves the disruption of the epidermis. Such conditions include the placement of a transdermal medical device, such as those disclosed in U.S. Pat. No. 5,207,652; including devices inserted through or across the skin at any naturally occurring or artificial orifice. One of skill in the art will recognize that the presently claimed hydrocolloid compositions can be used with any device which requires attachment to or through intact or damaged epidermis, exposed dermis or any mucosal surface of the body; these compositions of matter are useful for attaching medical or physiological monitoring devices to any surface, tissue or wound in mammals.

What is claimed is:

1. An adhesive formulation suitable for making a barrier disc, an adhesive pad or wound treatment pad, said formulation comprising:
   35–60% polyisobutylene,
   10–20% sodium alginate,
   10–20% pectin,
   5–10% gelatin,
   1–2% calcium silicate,
   5–10% of an absorptive agent selected from the group consisting of cellulose, methyl cellulose, propyl cellulose, carboxymethyl cellulose, hydroxyethyl cellulose, cellulose acetate, carbopol, karaya gum, tragacanth gum, guar gum, acacia gum, ghatti gum, xanthan gum, jaraya gum, locust bean gum, and psillium seed gum,
   0.5–2% calcium chloride,
   0.5–2% calcium phosphate,
   0.5–2% calcium sulphate, and
   0.1–0.5% magnesium borate.

2. An adhesive formulation suitable for making a barrier disc, an adhesive pad or wound treatment pad, said formulation comprising:
   35–60% acrylic adhesive,
   10–20% sodium alginate,
   10–20% pectin,
   5–10% gelatin,
   1–2% calcium silicate,
   5–10% of an absorptive agent selected from the group consisting of cellulose, methyl cellulose propyl cellulose, carboxymethyl cellulose, hydroxyethyl cellulose, cellulose acetate, carbopol, karaya gum, tragacanth gum, guar gum, acacia gum, ghatti gum, xanthan gum, jaraya gum, locust beam gum, and psillium seed gum,
   0.5–2% calcium chloride,
   0.5–2% calcium phosphate,
   0.5–2% calcium sulphate, and
   0.1–0.5% magnesium borate.

3. An adhesive formulation suitable for making a barrier disc, an adhesive pad or wound treatment pad, said formulation comprising:
   35–60% acrylic adhesive,
   10–60% sodium alginate,
   pectin,
   an absorptive agent selected from the group consisting of cellulose, methyl cellulose, propyl cellulose, carboxymethyl cellulose, hydroxyethyl cellulose, cellulose acetate, carbopol, karaya gum, tragacanth gum, guar gum, acacia gum, ghatti gum, xanthan gum, jaraya gum, locust beam gum, and psillium seed gum, and
   a setting agent comprising calcium chloride.

4. An adhesive formulation suitable for making a barrier disc, an adhesive pad or wound treatment pad, said formulation comprising:
   10–30% acrylic adhesive,
   10–30% polyisobutylene,
   15–20% sodium alginate,
   15–20% pectin,
   5–10% gelatin,
   1–2% calcium silicate,
   5–10% of an absorptive agent selected from the group consisting of cellulose, methyl cellulose, propyl cellulose, carboxymethyl cellulose, hydroxyethyl cellulose, cellulose acetate, carbopol, karaya gum, tragacanth gum, guar gum, acacia gum, ghatti gum, xanthan gum, jaraya gum, locust beam gum, and psillium seed gum,
   0.5–2% calcium chloride,
   0.5–2% calcium phosphate,
   0.5–2% calcium sulphate, and
   0.1–0.5% magnesium borate.

5. An adhesive formulation suitable for making a barrier disc, an adhesive pad or wound treatment pad, said formulation comprising:
   acrylic adhesive,
   10–20% sodium alginate,
   10–20% pectin,
   5–10% gelatin,
   1–2% calcium silicate,
   5–10% of an absorptive agent selected from the group consisting of cellulose, methyl cellulose, propyl cellulose, carboxymethyl cellulose, hydroxyethyl cellulose, cellulose acetate, carbopol, karaya gum, tragacanth gum, guar gum, acacia gum, ghatti gum, xanthan gum, jaraya gum, locust beam gum, and psillium seed gum, 0.5–2% calcium chloride, 0.5–2% calcium phosphate, 0.5–2% calcium sulphate, and 0.1–0.5% magnesium borate.

6. An adhesive formulation suitable for making a barrier disc, an adhesive pad or wound treatment pad, said formulation comprising:

acrylic adhesive, sodium alginate, pectin, an absorptive agent selected from the group consisting of cellulose, methyl cellulose, propyl cellulose, carboxymethyl cellulose, hydroxyethyl cellulose, cellulose acetate, carbopol, karaya gum, tragacanth gum, guar gum, acacia gum, ghatti gum, xanthan gum, jaraya gum, locust beam gum, and psillium seed gum, a setting agent comprising 0.5–2% calcium chloride, and mineral oil.

7. An adhesive formulation suitable for making a barrier disc, an adhesive pad or wound treatment pad, said formulation comprising:

25% acrylic adhesive,

25% polyisobutylene,

20% sodium alginate,

14% pectin,

4% gelatin, 1.75% calcium silicate,

5% of an absorptive agent selected from the group consisting of cellulose, methyl cellulose, propyl cellulose, carboxymethyl cellulose, hydroxyethyl cellulose, cellulose acetate, carbopol, karaya gum, tragacanth gum, guar gum, acacia gum, ghatti gum, xanthan gum, jaraya gum, locust beam gum, and psillium seed gum, 2% calcium chloride, 2% calcium phosphate, 1% calcium sulphate, and 0.25% magnesium borate.

8. An adhesive formulation suitable for making a barrier disc, an adhesive pad or wound treatment pad, said formulation comprising:

25% acrylic adhesive,

25% polyisobutylene,

10% sodium alginate,

10% pectin,

5% gelatin,

4% calcium silicate,

20% of an absorptive agent selected from the group consisting of cellulose, methyl cellulose, propyl cellulose, carboxymethyl cellulose, hydroxyethyl cellulose, cellulose acetate, carbopol, karaya gum, tragacanth gum, guar gum, acacia gum, ghatti gum, xanthan gum, jaraya gum, locust beam gum, and psillium seed gum, 0.25% calcium chloride, 0.25% calcium phosphate, 0.25% calcium sulphate, and 0.25% magnesium borate.

9. A two-component liquid adhesive, wherein said adhesive is biocompatible and cures to a firm, flexible solid, said adhesive being suitable for adhering medical devices to skin, said adhesive comprising Component A and Component B, wherein (A) Component A comprises 40–80% sodium alginate, and wherein Component A has a viscosity in the range of 85–115 poise in aqueous solution; and (B) Component B is an emulsion which comprises low molecular weight liquid acrylic adhesive, low molecular weight polyisobutylene, a setting agent comprising calcium chloride, and gelatin.

10. A two-component liquid adhesive, wherein said adhesive is biocompatible and cures to a firm, flexible solid, said adhesive being suitable for adhering medical devices to skin, said adhesive comprising Component A and Component B, wherein (A) Component A comprises sodium alginate and low molecular weight polyisobutylene, and (B) Component B comprises an aqueous medium having total solutes and suspended particles to yield a viscosity exceeding 75 poise wherein said solutes comprise a setting agent comprising calcium chloride, pectin, and an absorptive agent selected from the group consisting of cellulose, methyl cellulose, propyl cellulose, carboxymethyl cellulose, hydroxyethyl cellulose, and cellulose acetate.

11. The adhesive formulation of claim 3, further comprising up to 60% gelatin, up to 5% calcium silicate, up to 10% calcium phosphate, up to 10% calcium sulphate, and up to 0.5% magnesium borate.

12. The adhesive formulation of claim 5, further comprising up to 60% polyisobutylene.

13. The adhesive formulation of claim 6, further comprising up to 60% polyisobutylene up to 20% gelatin, up to 10% calcium silicate, up to 10% calcium phosphate, up to 10% calcium sulphate, up to 0.5% magnesium borate, up to 10% povidone iodine, and up to 2% benzalkonium chloride.

14. The two-component liquid adhesive of claim 9, wherein Component A further comprises up to 30% of one selected from the group consisting of calcium-free carboxymethyl cellulose or cellulosic derivatives, and wherein Component B further comprises up to 10% calcium sulphate, up to 5% calcium silicate, up to 10% calcium phosphate, and up to 1.5% magnesium borate.

15. The two-component liquid adhesive of claim 10, wherein Component A further comprises up to 95% low molecular weight acrylic adhesive, and wherein said solutes of Component B further comprise up to 10% calcium sulphate, up to 5% calcium silicate, up to 10% calcium phosphate, up to 2.5% magnesium borate, and up to 40% gelatin.

* * * * *